United States Patent [19]

Walsh

[11] Patent Number: 5,583,298
[45] Date of Patent: Dec. 10, 1996

[54] METHOD AND APPARATUS FOR ON-LINE TESTING OF PULTRUDED STOCK MATERIAL

[75] Inventor: Shawn Walsh, Boston, Mass.

[73] Assignee: The United States of America as represented by the Secretary of the Army, Washington, D.C.

[21] Appl. No.: 433,553

[22] Filed: Apr. 24, 1995

[51] Int. Cl.6 .................................................. G01N 3/20
[52] U.S. Cl. .............................................. 73/852; 73/831
[58] Field of Search ........................ 73/788, 828, 829, 73/831, 841, 852, 855, 856, 865.8, 866.5

[56] References Cited

U.S. PATENT DOCUMENTS

| | | | |
|---|---|---|---|
| 2,506,048 | 5/1950 | Van Den Akker | 73/852 |
| 3,194,063 | 7/1965 | McKean | 73/852 |
| 4,213,349 | 7/1980 | Miura | 73/852 |
| 4,562,743 | 1/1986 | Bonine | 73/828 |
| 4,583,407 | 4/1986 | LeGrand et al. | 73/852 |
| 5,503,024 | 4/1996 | Bechtel et al. | 73/852 |

Primary Examiner—Richard Chilcot
Assistant Examiner—Max H. Noori
Attorney, Agent, or Firm—Freda L. Krosnick; Muzio B. Roberto

[57] ABSTRACT

The invention is directed to a method and apparatus for testing the quality of pultruded material by measuring a load applied to the material as it is being pultruded and measuring the load associated with a fixed displacement of the pultruded stock material.

9 Claims, 5 Drawing Sheets

FIBER MATERIAL

| PROPERTY | BORON | A84 GRAPHITE | GY-70 GRAPHITE | KEVLAR 49 | S GLASS | SPECTRA 900 |
|---|---|---|---|---|---|---|
| COEFFICIENT OF AXIAL THERMAL EXPANSION (10⁶/°C) | 16 | -0.4 | -1.1 | -0.1 | 5 | -15 |
| COEFFICIENT OF TRANSVERSE THERMAL EXPANSION (10⁶/°C) | 16 | 18 | 18 | 64 | 5 | 135 |
| AXIAL TENSILE MODULUS (MSI) | 60 | 34 | 75 | 19 | 12 | 13 |
| TRANSVERSE TENSILE MODULUS (MSI) | 60 | 2 | 1 | 1 | 12 | 0.5 |
| MAJOR POISSON'S RATIO | 0.13 | 0.20 | 0.20 | 0.33 | 0.22 | 0.19 |
| LONGITUDINAL SHEAR MODULUS (MSI) | 24 | 4 | 3 | 3 | 5 | 0.3 |
| AXIAL TENSILE STRENGTH (KSI) | 500 | 520 | 250 | 525 | 600 | 400 |
| TRANSVERSE TENSILE STRENGTH (KSI) | 50 | 30 | 25 | 25 | 600 | 25 |
| LONGITUDINAL SHEAR STRENGTH | 100 | 30 | 25 | 25 | 300 | 25 |

FIG. 6

| PROPERTY | MATRIX MATERIAL | | | | | |
|---|---|---|---|---|---|---|
| | ALUMINUM ALLOY 2024-T4 | HERCULES 3501-6 EPOXY | HEXCEL F155 RUBBER-TOUGHENED EPOXY | HERCULES 4001 BISMALE-IMIDE | ICI VICTREX PEEK THERMO-PLASTIC |
| COEFFICIENT OF THERMAL EXPANSION ($10^{-6}/°C$) | 25 | 41 | 63 | 53 | 51 |
| COEFFICIENT OF MOISTURE EXPANSION ($10^{-3}/M$) | 0 | 3.2 | 3.1 | 2.3 | 9 |
| TENSILE MODULUS (MSI) | 10 | 0.62 | 0.45 | 0.52 | 0.59 |
| POISSON'S RATIO | 0.33 | 0.34 | 0.41 | 0.44 | 0.28 |
| SHEAR MODULUS (MSI) | 3.8 | 0.23 | 0.15 | 0.18 | 0.23 |
| TENSILE STRENGTH (KSI) | 70 | 8.8 | 11.2 | 7.7 | 7.8 |
| SHEAR STRENGTH (KSI) | 40 | 14.7 | 7.0 | 5.8 | 10.4 |

FIG. 7

METHOD AND APPARATUS FOR ON-LINE TESTING OF PULTRUDED STOCK MATERIAL

FIELD OF THE INVENTION

The invention relates to the testing of pultruded stock materials during manufacture.

BACKGROUND OF THE INVENTION

There is a need in the art to develop effective and useful non-destructive methods for testing various materials, as for example, pultruded stock material. Test methods in the prior art used sonic, ultrasonic and modal (non-destructive) analysis, as well as, four-point bending and short beam shear (destructive) mechanical tests.

However, there were problems with the aforementioned non-destructive methods. First, they were principally detecting fiber dominated properties. Consequently, the matrix dominated properties, which reflect more fully the influence of processing were being monitored secondarily. Second, implementation of the non-destructive methods was complicated by factors that included the following: non-uniform (three-dimensional) temperature gradients, noise-affected signals (e.g., electrical machinery and vibration from equipment), and the problem of sustainable boundary conditions on the ends of sampled pultruded specimens. Collectively, these influences provided only a marginal determination of property variation. Once error bounds were applied, differentiation due to processing become particularly difficult to assert with confidence.

The herein disclosed invention seeks to eliminate problems encountered by prior art test methods.

OBJECTS OF THE INVENTION

An object of this invention is to develop an efficient on-line, non-destructive method of testing pultruded stock material.

A further object is to develop a method of testing material with variety of cross-sections.

An additional object is to develop a method which lends itself to on-line test sensors.

SUMMARY OF THE INVENTION

The invention herein disclosed seeks to overcome the limitations of the test procedures set forth above. The test procedure of the instant invention is designed to be sensitive to both fiber and matrix dominated properties.

The test method of the invention provides a means and method for assessing how the quality of continuously pultruded stock varies as a result of processing conditions upstream in the pultrusion process. Upstream conditions include, but are not limited to, resin bath viscosity variations, fiber placement and uniformity, temperature and pressure distributions present in the heated forming die, and pulling force.

Several advantageous features are incorporated into this invention.

First, the method used to obtain the property measurements can be deployed over a variety of pultruded specimens of constant cross-section. That is, the pultruded specimen may have a complex geometric cross-section, but since the invention monitors variations in the measured properties such complex cross-section geometries can be readily accommodated.

Second, the concept of continuously measuring property variation by means of fixed displacement and rollers allows for on-line measurement of bulk property variations. This information can then be used to enhance both the quality of the pultruded part and performance of the pultruder system itself.

Third, the use of supplemental sensors such as LVDTs and thermocouples permits on-line compensation for extraneous variations in dimensional stability and temperature, respectively.

Fourth, two distinct sets of equations have been developed for relating variations in the observed load to the variations in the bulk mechanical response of the composite; the first is a Young's modulus measurement and the second is a shear modulus measurement.

Fifth, the design of the invention allows for the-novelty of obtaining either a flexural measurement or torsional measurement, depending on the roller configuration at the point on the pultruded beam where the load or torque is applied.

Sixth, this invention permits non-destructive, continuous measurements and is immune to the noise and related problems associated with other non-destructive measurement techniques and devices, such as ultrasound.

Seventh, the invention is, by design, adaptive so that it may accommodate a variety of pultruded stock. This includes the use of various resin and fiber systems, die geometries, surface treatments, and the like.

The invention herein disclosed involves the testing of pultruded stock or composite material by measuring the characteristic of the material by measuring the Young's modulus and/or the shear modulus of the material being processed. Determinations have been made to determine whether or not deliberate variations in the processing of pultruded stock would manifest themselves as variations in the mechanical properties that developed in the pultruded material. For example, the pultruder die temperature was varied and the subsequent stock produced was marked, cut, and later tested off-line. These tests included the use of sonic, ultra-sonic, and modal (non-destructive) analyses, as well as four-point bending and short beam shear (destructive) mechanical tests. The destructive mechanical tests served to corroborate the variations in properties detected with the non-destructive tests. The conclusion from this study was that one could, in fact, use non-destructive methods (e.g. load deflection) for detecting mechanical property variations due to perturbations (either naturally occurring or artificially induced) in the pultruded stock.

The invention measures beam deflection caused by an imposed load. In the operation of this invention, the adjustment of the span over which the load is applied minimizes the effects of body forces (such as the beam's own weight). Furthermore, by imposing and maintaining zero deflection and zero slope (i.e., "built in") boundary conditions on both ends of the pultruded beam, one imposes a fixed displacement at the center of the span and measures the corresponding load. Over small displacements, the relationship between load and displacement of this type is typically linear. The line speed associated with pultrusion (i.e., the velocity with which solidified, composite material is pulled through the heated die) is relatively low and kept fairly constant; thus inertial loadings and effects are neglected. Furthermore, a properly designed apparatus involving the use of rollers makes it possible to continuously measure variations in load due to the fixed displacement applied to the pultruded stock.

Thus, for the first time, it is possible to have an on-line device for monitoring bulk mechanical property variations as a function of upstream processing conditions. Such a device has the potential to ensure and improve product quality, minimize start-up time, eliminate waste, identify critical processing parameters and processing windows for a variety of materials, and ultimately aid in "closing the loop" for intelligent process control.

The method and apparatus suggested by this invention could potentially find application in a variety of continuous processing systems. For example, extruded stock of constant cross section could be monitored for consistency of similar material properties.

The invention (shown generally in FIGS. 1 and 2) consists of a series of adjustable, rigid rollers aligned such that pultruded stock is physically displaced by a fixed and measurable amount. The force or torque (i.e., the load) associated with this fixed displacement is simultaneously measured by means that include strain gages, force transducers, and torque indicators. FIG. 1 illustrates the location of components, relative to the pultruder. As shown pultruded stock enters a first set of rollers and exits at a set of identical rollers; this configuration continuously maintains a zero displacement and a zero slope condition on either end of the beam portion under measurement. The flexural or torque load is applied at the center span of the beam, as shown in FIG. 1. FIG. 2 illustrates the kind of data obtained from on-line sensor measurements, and is typical of that which might appear on a computer monitor and system dedicated to retrieving and displaying the data. Two basic measurements can be made, depending on the configuration of the roller system: Young's modulus and shear modulus.

Young's modules (previously mentioned) principally referenced as "E" in the mechanics literature, is a well known quantity and represents the "stiffness" of a material. In the case of composite materials, the stiffness depends on both the reinforcement and matrix properties, as well as the fiber volume fraction present; this can be expressed generally as:

$$E_{composite} = f(E_{reinforcement}, E_{matrix}, V_f)$$

For example, for a unidirectional composite (typically produced by the pultrusion process) the composite modulus can be calculated using a rule of mixtures approach:

$$E_{composite} = E_r V_f + E_m(1-V_f)$$

An important distinction in the application of this equation, as it applies to the present invention, is the principal assumption of fiber uniformity in the cross-section of the pultruded material. When a bending stiffness is measured it is well known that the measurement is particularly sensitive to surface properties, as compared to properties measured towards the center of a composite. That is, fiber rich areas occurring well away from the neutral axis of a given piece of pultruded stock would tend to reflect a higher observed stiffness as compared to a resin rich surface. The present invention allows one to observe how fiber variation through the thickness of pultruded stock influences the measured mechanical property.

Shear Modulus (previously mentioned) is another important property in the description of the mechanical behavior of a material. If one is particularly interested in how variations in the pultrusion die influences the development of properties in the stock, monitoring variations in the composite shear modulus is recommended in lieu of Young's modulus measurements. The shear modulus measurement is substantially more sensitive to variations in the matrix properties than the bending stiffness measurement.

On-line Flexural Measurement Method

An equation is required for relating variations in load resulting from variations in modulus. Assuming a fixed displacement (i.e., Δ=constant), and assuming further that the load is applied at the center of the pultruded stock span, the following relation is obtained:

$$\Delta_{max} = \frac{PL^3}{192EI}$$

In this equation, $\Delta$ is the displacement, P is the applied load, L is the span of the pultruded stock undergoing measurement, E is Young's modulus, and I is the moment of inertia. This equation is applicable if the variation in fiber distribution is modest, material properties are uniform through the cross-section of the pultruded stock, and the stock has achieved a quasi-steady state insofar as the material properties entering and exiting the span over which measurements are made.

On-line Torsional Measurement Method

Equilibrium $M_A$, $M_B$, and $M_C$ are the moments associated with a load applied at a point B along the pultruded span; points A and B are associated with zero displacement/zero slope conditions maintained at either end of the pultruded beam by the rollers and $M_C$ is the moment associated with the applied torque; thus:

$M_A + M_B - M_C = 0$
Geometric Compatibility
$\phi_{BC} = \phi_{AB}$
Load Deformation Relation $$\phi_{AB} = \frac{M_A L_{AB}}{G_S[cab^3]}$$

$$\phi_{BC} = \frac{M_B L_{BC}}{G_S[cab^3]}$$

In these last two relations (i.e., $\phi_{AB}$ and $\phi_{BC}$) an important and well known approximation was used. This approximation was developed in order to provide a means for describing the torsional behavior of rectangular shafts by Timoshenko and Goodier, and assumes the following general form:

$$\phi = \frac{ML}{G_S[cab^3]}$$

In this equation c is a coefficient, arrived at by advanced theoretical analysis of a moment being applied to a generally rectangular bar; the coefficient c depends upon the aspect ratio of the shaft. This dependence is tabulated below and plotted in FIG. 3.

| a/b | c |
| --- | --- |
| 1 | 0.141 |
| 1.5 | 0.196 |
| 2 | 0.229 |
| 3 | 0.263 |
| 5 | 0.291 |
| 10 | 0.312 |

There are a sufficient number of equations to resolve the relation of applied torque to the resulting deformation. Assuming that the torque is applied at the middle of the rectangular pultruded bar stock (i.e., $L_{AB}=L_{BC}$) the following relation is obtained:

$$\phi = \frac{M_C L_{AB}}{G_S[cab^3]}$$

Thus, if $\phi$ remains fixed this last equation can be used to relate variations in the corresponding applied moment to the composite shear modulus. If one assumes (reasonably) that the fiber properties change relatively little during the pultrusion process one can then relate the composite modulus, $G_S$, to the matrix modulus $G_M$. One such relation is the Halpin-Tsai model:

$$\frac{G_S}{G_M} = \frac{1+\xi\eta V_f}{1-\eta V_f}$$

where $$\eta = \frac{(G_f/G_m)-1}{(G_f/G_m)+\xi}$$

Typical properties for $G_f$ and $G_m$ for a variety of fibers and matrix systems are given in FIGS. 6 and 7, respectively.

FIG. 4 illustrates how increasing the composite shear modulus affects the matrix modulus. FIG. 5 demonstrates that a % change in the composite shear modulus has a correspondingly higher % change in the matrix shear modulus. For example, the present invention would detect a 25% change in the composite modulus indicating that the matrix change may be as much as 52% due to upstream process variations. Collectively, these equations would aid in determining how upstream process variations influence the development of the composite properties, and more specifically, the matrix properties.

In an embodiment of this invention pultruded stock material is tested by fixing a longitudinal section of the pultruded stock material between two fixed points, imposing a load on the pultruded stock material held between said two fixed points and measuring the load associated with a fixed displacement of the pultruded stock material. The load applied can be applied perpendicular to the plane of pultruded stock material or it can be applied by torque. Alternatively, the load can be a sheer load.

In an alternative embodiment, a specific load is applied to the material between the two fixed points and the displacement of the pultruded stock material relative to the specific load is measured. In a unique embodiment the displacement is measured by the displacement angle of the pultruded material at one of the two fixed points.

An apparatus for carrying out the methods set forth above comprises in a combination a pultrusion device, a means for retaining pultruded stock material between two fixed points, a means for applying a load to pultruded stock material positioned between said two fixed points and a means for determining the force or load associated with a fixed displacement of the pultruded stock material.

Pressure applied to the rollers can serve to fix the pultruded material for testing.

Means for determining applied force or load are well known in the art.

The load to be applied in the apparatus can be a load applied perpendicularly to the plane of the pultruded stock material or the load can be applied as torque or sheer load.

In the disclosed invention the pultruded material is fixed by the rollers, however any means which can hold the pultruded material in a fixed position would be operative.

It is obvious that while the above disclosed invention measures a load associated with a fixed displacement of pultruded stock material; measurement could be based on the amount of displacement of the pultruded stock material based on a fixed load.

It is also obvious that measurements are to be compared to established standards for the material being pultruded.

BRIEF DESCRIPTION OF THE DRAWINGS

FIGS. 6 and 7 are tables of typical $G_f$ and $G_m$ properties of a variety of fibers and matrix systems.

GENERAL DESCRIPTION OF THE PREFERRED EMBODIMENTS

Figure 1:
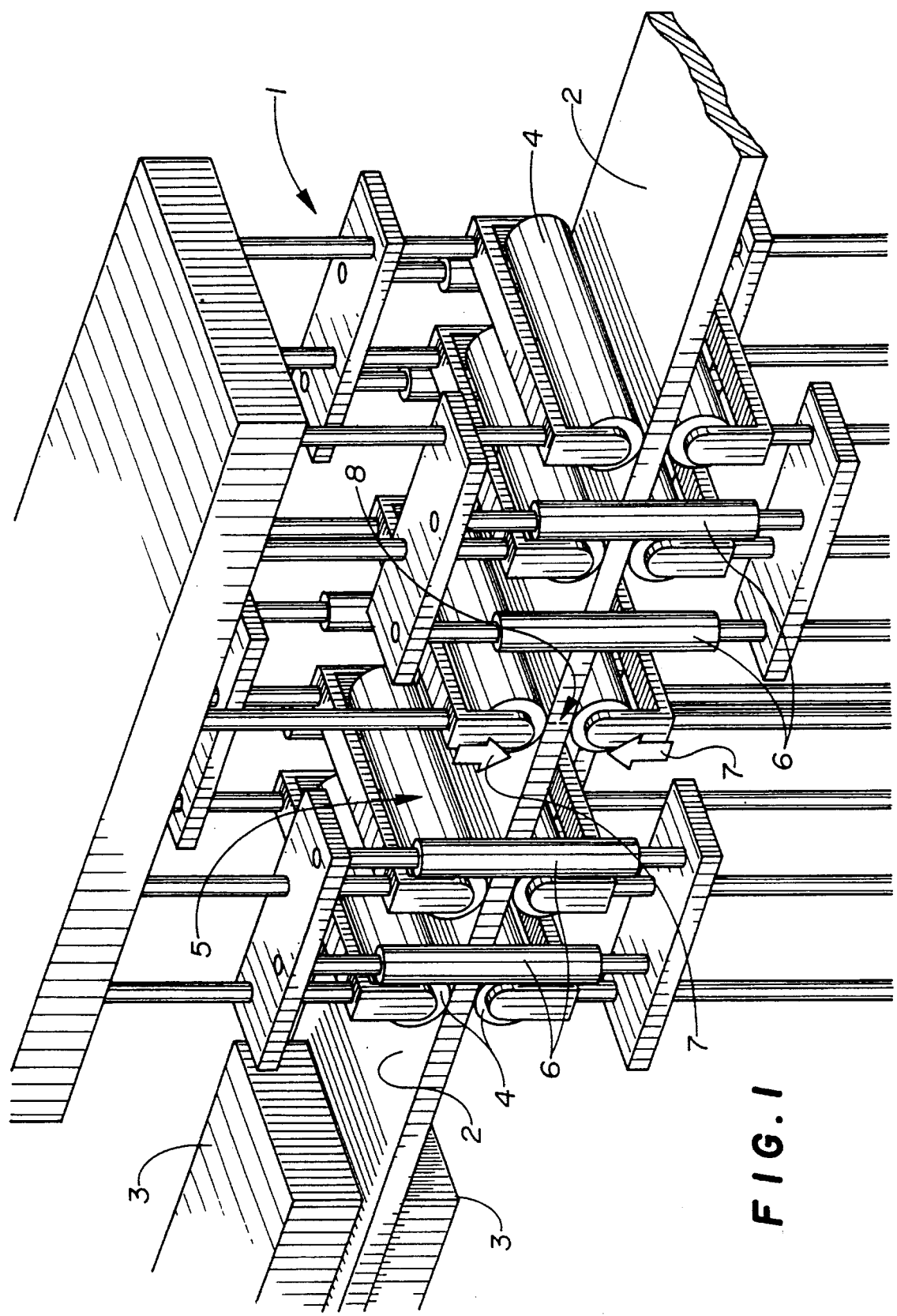
FIG. 1 is a view illustrating the pultruder test device for testing pultruded stock material.
Figures 2, 3:
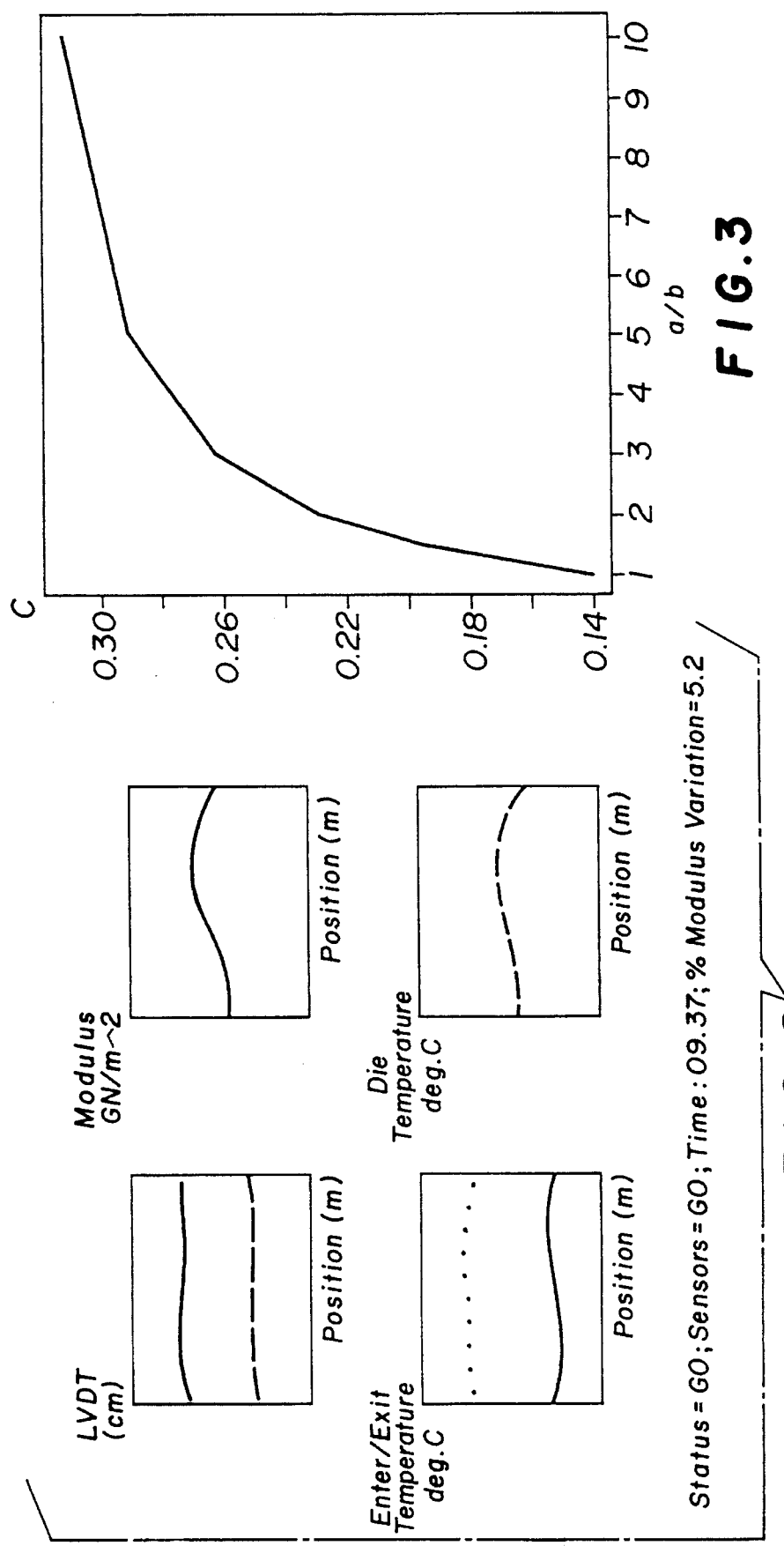
FIG. 2 illustrates data obtained from on-line sensor measurements.
FIG. 3 plots the dependence of coefficient C on the aspect ratio of the torsional behavior of rectangular shafts.
Figure 5:
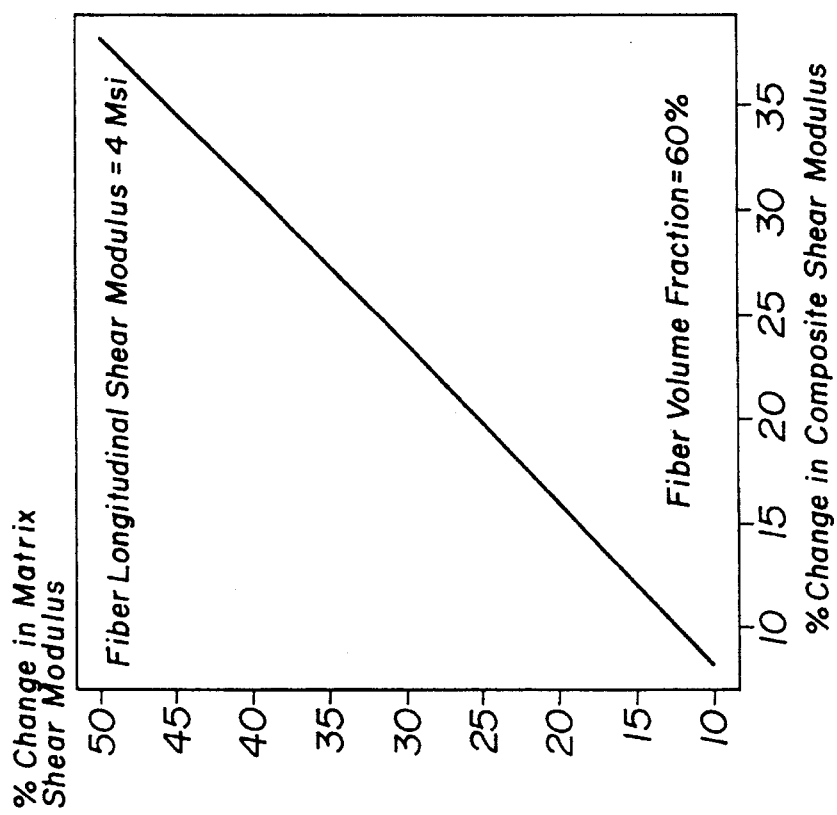
FIG. 5 demonstrates that a percentage change in the composite shear modulus has a correspondingly higher percentage change in the matrix shear modulus.
Figure 4:
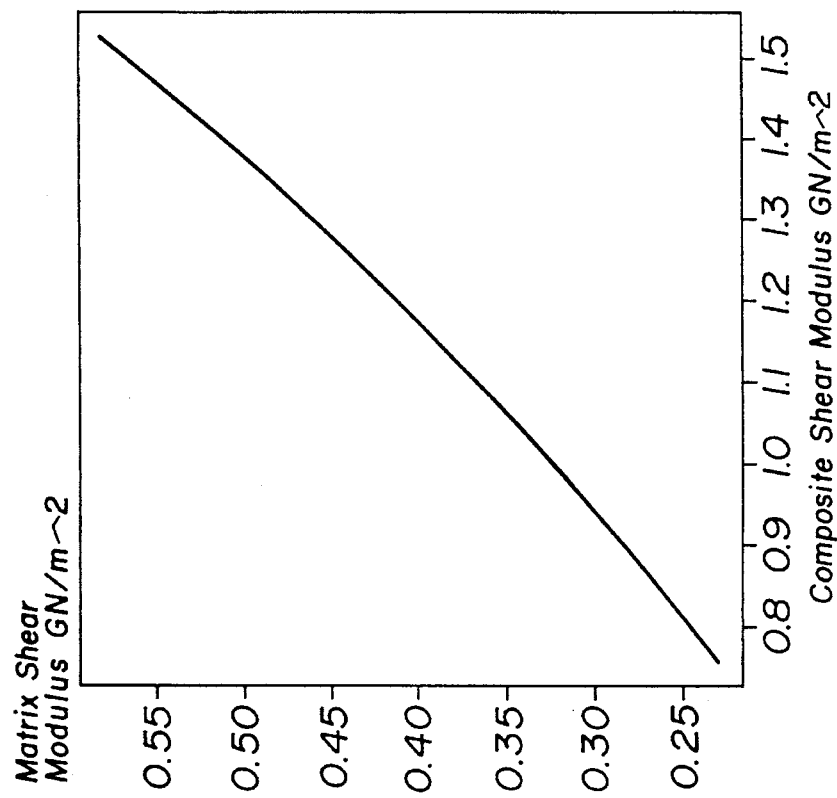
FIG. 4 illustrates how increasing the composite shear modulus affects the matrix modulus.

With reference to FIG. 1 an apparatus for testing pultruded stock material 1 tests a section of pultruded stock material 2. The pultruded stock material 2 is pultruded using pullers 3 and is run through a series of adjustable, rigid rollers 4. These rollers 4 at the time of testing fixedly maintain a zero displacement and zero slope conditions on either end 5 of the pultruded stock material 2 under measurement. Tension on the rollers is maintained by hydraulic pistons 6. Load 7 is applied which can be either flexural, shear or torque. With the load 7 applied at the center span 8 of the pultruded stock material 2 the displacement caused by the load 7 is measured. If the load 7 applied produces a deviation from established standards, the process conditions are adjusted to make the pultruded product conform to standard.

Many advantages are envisioned by the use of this invention. For example, the test of this invention are non-destructive. The tests can be performed on-line, and process conditions can be adjusted based on the test results. Any number and types of pultruded materials can be tested and the tests can be employed on samples with complex geometric cross-section. Flexural or torsional measurements can be advantageously used in the testing procedure. Clearly, the test described herein is a significant advance in the field of pultruded stock material manufacture.

What is claimed is:

1. A method for measuring the composite mechanical properties of a polymer-based pultruded stock consisting of two or more resin or fiber material during the manufacture of said pultruded stock comprising the steps of:

a) selecting a pultruded stock material, b) positioning a longitudinal section of the pultruded stock material between two fixed points on a series of adjustable, rigid rollers, c) imposing a load on the pultruded stock material, d) allowing the rollers to adapt to the geometric and mechanical constraints of the pultruded stock, e) providing continuous support on either end of the test section to allow the pultruded stock to flow through freely and continuously, f) continuously maintaining a zero displacement and a zero slope condition on either end of the beam portion under measurement thereby imposing a fixed displacement at the center of the span, and g) measuring the imposed load associated with a specific displacement of the pultruded stock material.

2. The method of claim 1 wherein the imposed load is applied perpendicular to the plane of the pultruded stock material.

3. The method of claim 1 wherein the imposed load is applied by torque.

4. The method of claim 1 wherein the imposed load is a shear load.

5. The method of claim 1 wherein the displacement is measured by the displacement angle of the pultruded material at one of the two fixed points.

6. An apparatus for continuously measuring the composite mechanical properties of a polymer-based pultruded stock comprising of two or more resin or fiber materials during the manufacture of said pultruded stock comprising:

puller means, a series of horizontally positioned adjustable, roller means, the puller means are designed to be compatible with the roller means in transporting the pultruded stock through the system, hydraulic piston means designed to apply pressure to the roller means at the center span, so that on the application of a load at the center span of the pultruded stock, the displacement caused by the load is measured.

7. The apparatus for testing pultruded stock material of claim 1 wherein the means for applying the load applies a load perpendicular to the plane of the pultruded stock material.

8. The apparatus for testing pultruded stock material of claim 1 wherein the load is applied by torque.

9. The apparatus for testing pultruded stock material of claim 1 wherein the load is a shear load.

* * * * *